US009194931B2

(12) United States Patent
Tsao et al.

(10) Patent No.: US 9,194,931 B2
(45) Date of Patent: Nov. 24, 2015

(54) LENGTH MEASUREMENT METHOD AND DEVICE OF THE SAME

(71) Applicant: Wistron Corp., New Taipei (TW)

(72) Inventors: Wen-Chun Tsao, New Taipei (TW); Yao-Tsung Chang, New Taipei (TW); Chia-Hsien Li, New Taipei (TW)

(73) Assignee: WISTRON CORP., New Taipei (TW)

( * ) Notice: Subject to any disclaimer, the term of this patent is extended or adjusted under 35 U.S.C. 154(b) by 4 days.

(21) Appl. No.: 14/259,954

(22) Filed: Apr. 23, 2014

(65) Prior Publication Data

US 2015/0153158 A1 Jun. 4, 2015

(30) Foreign Application Priority Data

Nov. 29, 2013 (TW) .............................. 102143886 A

(51) Int. Cl.
*G01C 1/04* (2006.01)
*G01B 11/02* (2006.01)
*G01S 5/00* (2006.01)
*G01C 3/08* (2006.01)
*G01C 15/00* (2006.01)

(52) U.S. Cl.
CPC ...... *G01S 5/00* (2013.01); *G01C 3/08* (2013.01); *G01B 11/02* (2013.01); *G01C 1/04* (2013.01); *G01C 15/002* (2013.01)

(58) Field of Classification Search
CPC ....... G01B 11/022; G01B 11/02; G01B 21/02; G01C 15/002; G01C 1/04; G01C 11/04
USPC .................................................. 356/600–640
See application file for complete search history.

(56) References Cited

U.S. PATENT DOCUMENTS 3,191,170 A * 6/1965 Lustig et al. ................. 342/191
4,727,374 A * 2/1988 Boulais .......................... 342/50
(Continued)

FOREIGN PATENT DOCUMENTS

JP H11-304424 A 11/1999
TW 200817651 A 4/2008
(Continued)

OTHER PUBLICATIONS

TW Office Action dated Mar. 25, 2015 as received in Application No. 102143886 (English Abstract).

*Primary Examiner* — Gregory J Toatley
*Assistant Examiner* — Jarreas C Underwood
(74) *Attorney, Agent, or Firm* — Maschoff Brennan

(57) ABSTRACT

The present invention proposes a length measurement method and a length measurement device. The length measurement method includes steps of emitting the laser via a laser ranging module in a reference direction to order to detect a reference distance between a reference point on a target and the laser ranging module, taking the reference direction as a the measurement direction, taking the reference distance as a first distance, executing a border detecting procedure according to the measurement direction and the first distance in order to detect a border of the target, and calculating measurement distance between the border and the reference point according to border location information of the laser ranging module corresponding to the border, the reference direction and the reference distance.

16 Claims, 13 Drawing Sheets

(56) References Cited

U.S. PATENT DOCUMENTS

| | | | |
|---|---|---|---|
| 5,616,903 A * | 4/1997 | Springer | 235/414 |
| 6,281,968 B1 * | 8/2001 | Seifert et al. | 356/3.03 |
| 7,319,512 B2 * | 1/2008 | Ohtomo et al. | 356/4.03 |
| 7,656,508 B2 * | 2/2010 | Iwaki et al. | 356/4.03 |
| 7,764,809 B2 * | 7/2010 | Ohtomo et al. | 382/106 |
| 7,893,947 B2 * | 2/2011 | Fang | 345/613 |
| 8,164,628 B2 * | 4/2012 | Stein et al. | 348/148 |
| 2011/0043682 A1 | 2/2011 | Chou et al. | |
| 2011/0075159 A1 | 3/2011 | Chang et al. | |

FOREIGN PATENT DOCUMENTS

| | | |
|---|---|---|
| TW | 201107856 A1 | 3/2011 |
| TW | 201139977 A1 | 11/2011 |
| TW | 201312080 A1 | 3/2013 |
| WO | 2013/059599 A1 | 4/2013 |

* cited by examiner

LENGTH MEASUREMENT METHOD AND DEVICE OF THE SAME

CROSS REFERENCE

The present application is based on, and claims priority from, Taiwan Application Serial Number 102,143,886, filed on Nov. 29, 2013, the disclosure of which is hereby incorporated by reference herein in its entirety.

BACKGROUND

1. Field

The present invention relates a length measurement method and a device of the same, more particularly, to a ranging-principle applied length measurement method and a device of the same.

2. Related Art

When taking physical exams, height is a required measurement in order to calculate body mass index (BMI). However a conventional height measurement device using physical element (e.g. a plate) to determine a head height. In order to be adaptive for different heights, the conventional height measurement device is usually gigantic in size and therefore is not suitable for carrying. On the other hand, the conventional height measurement device can only measure one subject at a time and is time-consuming when measuring multiple subjects.

SUMMARY OF THE INVENTION

To address the aforementioned problems, the present invention provides a length measurement method and the length measurement device of the same. According to an embodiment of the present invention, a length measurement device calculates subject's height by detecting a distance between a subject and the length measurement device, and relative positioning of the subject's head and the length measurement device. According to another embodiment of the present invention, a length measurement device captures image containing one or more subjects and detects the distance between the subject and the length measurement device, and thereby calculates subject's height according to the image and the distance. Hence, according to the embodiments of the present invention, the volume of the length measurement device may be significantly decreased, and can therefore be easily carried and set up and dramatically shortens measurement time.

According to an embodiment of the present invention, a length measurement method includes steps of emitting the laser via a laser ranging module in a reference direction to order to detect a reference distance between a reference point on a target and the laser ranging module, taking the reference direction as a the measurement direction, taking the reference distance as a first distance, executing a border detecting procedure according to the measurement direction and the first distance in order to detect a border of the target, and calculating measurement distance between the border and the reference point according to a border corresponding to border location information of the laser ranging module, the reference direction and the reference distance.

According to an embodiment of the present invention, a length measurement device includes a laser ranging module and a control module. The control module is electrically connected to the laser ranging module. The control module includes a ranging unit, a border the detection unit and the calculation unit. The ranging unit is electrically connected to the laser ranging module, and arranged to control the laser ranging module emits the laser in the reference direction in order to detect a reference distance between a reference point on a subject and the laser ranging module. The border detection unit is electrically connected to the ranging unit, and arranged to take the reference direction as a the measurement direction, and the reference distance as a first distance, and to execute a border detecting procedure in order to detect the subject's border. The calculation unit is electrically connected to the ranging unit and the border detection unit, and arranged to calculate a measurement distance between the border and the reference point according to a border corresponding to border location information of the laser ranging module, the reference direction and the reference distance.

According to an embodiment of the present invention, a length measurement method includes steps of detecting a first measurement distance between a first subject and an image capturing device, using the image capturing device to capture measurement image containing the first subject, and calculating a first size of the first subject according to the first measurement distance and the measurement image.

According to an embodiment of the present invention, a length measurement device includes an image capturing module, a ranging module and a processing module. The image capturing module is arranged to capture measurement image containing the first subject. The ranging module is arranged to detect the first measurement distance between the first subject and the image capturing module. The processing module is electrically connected to the ranging module and the image capturing module, and arranged to calculate the first size of the first subject according to the first measurement distance and the measurement image.

In an embodiment of the present invention, the length measurement device detects the distance between the subject and the length measurement device and a relative positioning of the subject's head and the length measurement device, and calculates the subject's height. In another embodiment of the present invention, the length measurement device captures image containing the subject, and detects the distance between the subject and the length measurement device according to the image and the distance, and calculates the subject's height. Therefore, according to the embodiments of the present invention, the volume of the length measurement device may be significantly decreased and easily carried and set-up.

In order to make the aforementioned and other features of the present disclosure more comprehensible, several embodiments accompanied with figures are described in detail below.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION OF THE INVENTION

Figure 1:
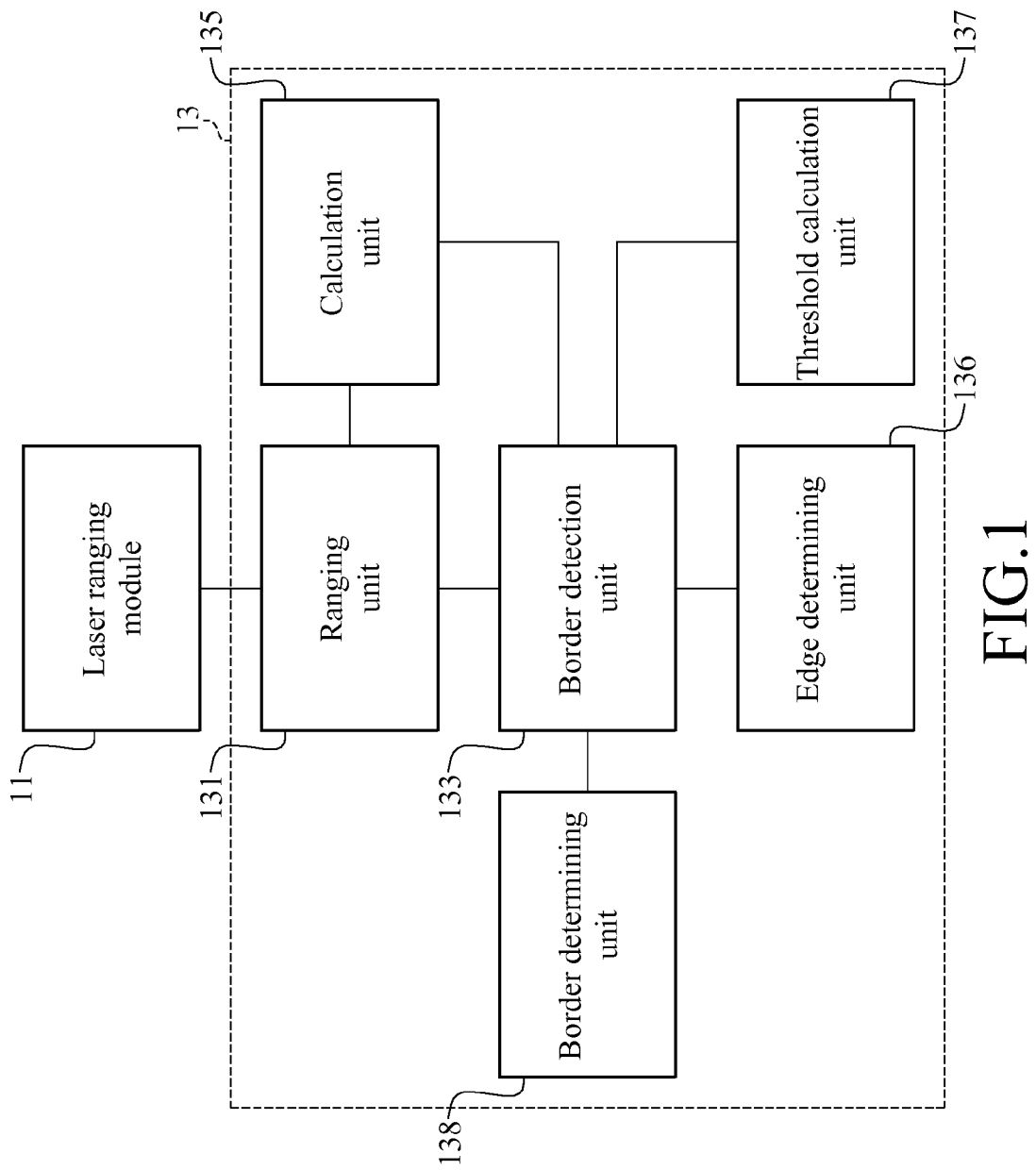
FIG. 1 is a block diagram illustrating a length measurement device according to an embodiment of the present invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Please refer to FIG. 1, which is a block diagram illustrating a length measurement device according to an embodiment of the present invention. As shown in FIG. 1, the length measurement device 1 includes a laser ranging module 11 and a control module 13. The control module 13 is electrically connected to the laser ranging module 11, and the control module 13 includes a ranging unit 131, a border detection unit 133 and a calculation unit 135, wherein the ranging unit 131 is electrically connected to the laser ranging module 11, the border detection unit 133 is electrically connected to the ranging unit 131, and the calculation unit 135 is electrically connected to the ranging unit 131 and the border detection unit 133.

The ranging unit 131 is arranged to control the laser ranging module 11 emits the laser in a reference direction for detecting a reference distance between a reference point on a subject and the laser ranging module 11. In this embodiment, the ranging unit 131 first resets the location of the laser ranging module 11 to a default location. Then the ranging unit 131 controls the laser ranging module 11 emits the laser in the subject. Due to the resetting of the location of the laser ranging module 11, laser emitted by the laser ranging module 11 may be horizontal in the subject. In other words, at this moment, the reference distance is also the horizontal distance between the laser ranging module 11 and the subject.

The border detection unit 133 is arranged to take the reference direction as the measurement direction, and the reference distance as a first distance. The border detection unit 133 executes a border detecting procedure in a first detecting direction to detecting the subject's border in the first detecting direction. For example, the border detection unit 133 may control the laser ranging module 11 emits the laser multiple times in the subject direction via the ranging unit 131, to detect multiple distances between the laser ranging module 11 and multiple points on and around the subject. The border detection unit 133 determines the subject's border according to these distances. In an embodiment, the subject is a user waiting for height measurement, the reference point may be the user's feet, and the border may be the user's head.

Figure 2:
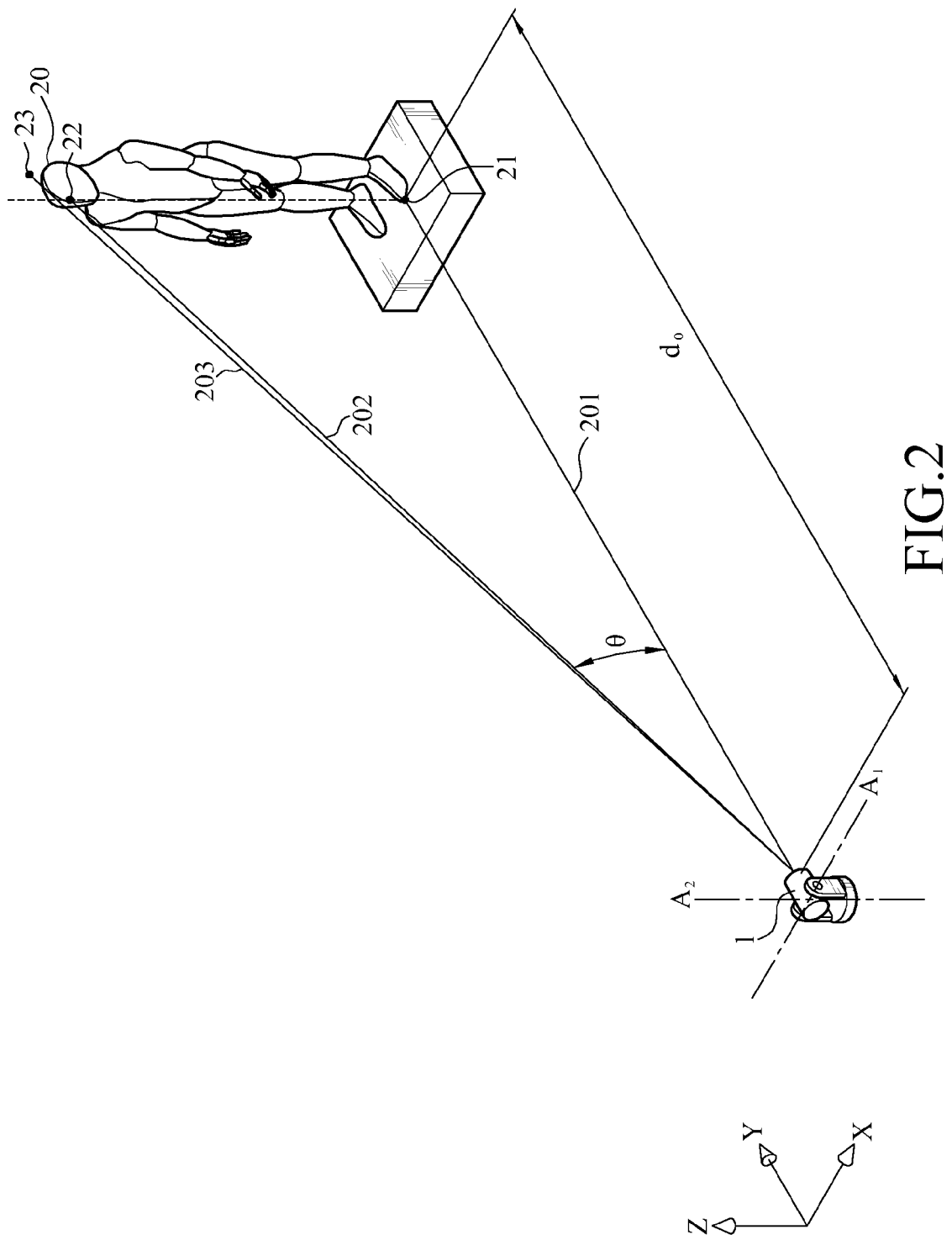
FIG. 2 is a schematic diagram illustrating operations of a length measurement device according to an embodiment of the present invention.

For example, please refer to FIG. 2, which is a schematic diagram illustrating operations of a length measurement device according to an embodiment of the present invention. As shown in FIG. 2, a user 20 uses the length measurement device 1 to measure his/her height. At first, the length measurement device 1 emits the laser to a reference point 21 on the user's feet in reference direction 201, and detects a reference distance $d_0$. Then the length measurement device 1 rotates a certain angle θ around a first axis A1 (the X axis in this embodiment) such that the measurement direction moves upward along the Z axis and the laser is emitted onto the user's body. In this embodiment, after the length measurement device 1 rotates angle θ several times and emits the laser onto a reflection point 22 on the user's forehead along a the measurement direction 202, the length measurement device 1 rotates angle θ again and emits the laser along the measurement direction 203. At this moment, the laser is emitted onto a reflection point 23 on a wall behind the user 20. At this moment, it may be determined that there is a edge between the measurement direction 202 and the measurement direction 203 due to the drastic change of the distance between the length measurement device 1 and the reflection point 23 regarding the distance between the length measurement device 1 and the reflection point 22, or the ratio of the distance between the length measurement device 1 and the reflection point 23 and the distance between the length measurement device 1 and the reflection point 22 being greater than a ratio threshold, and thus may select the reflection point 22 as an edge.

To be more specifically, the border detecting procedure may summarized as follows. In the beginning, there will be a first distance $d_1$ and the measurement direction. As mentioned above, the initial first distance $d_1$ and measurement direction are the reference distance $d_0$ and the reference direction, respectively. The measurement direction is rotated a first angle θ around a first axis A1 along the first detecting direction (upward). The laser ranging module 11 emits the laser onto a first reflection point in the rotated measurement direction, for detecting the distance between the first reflection point and the laser ranging module 11. The distance between the first reflection point and the laser ranging module is used as a second distance d2. Whether the subject's edge is detected is determined according to the second distance d2. If the edge is detected, the border is determined according to the edge. If the edge is not detected, take the second distance d2 as the first distance $d_1$, and the border detecting procedure is continued in the first detecting direction to detect the subject's border.

After the border is determined according to the edges, the calculation unit 135 is arranged to calculate the distance between the measurement border and reference point according to the border corresponding to border location information of the laser ranging module, reference direction and reference distance. For example, if it were to measure the subject's height, when the border location information only contains the border distance corresponding to the laser ranging module 11, it is assumed that the subject's surface is smooth and perpendicular to the ground. According to the Pythagorean theorem, if the reference direction is paralleled to the ground, the right triangle's height (i.e., the opposite side) may be calculated according to the following equation: hypotenuse$^2$-adjacent side$^2$=opposite side$^2$, given that the border distance is the hypotenuse, and the reference distance is the adjacent side.

In another example, if it were to measure the subject's height, when border location information only contains the border angle corresponding to the laser ranging module 11 and the border, and the reference direction is paralleled to the ground, it is assumed that the subject's surface is smooth and perpendicular to the ground. If the reference direction paralleled to the ground, the subject's height equals the reference distance multiplying the value of tangent function of the border angle according to the definition of the tangent function.

In some examples, if the reference direction, the border direction and the connection line between the reference point on the subject's surface and the border does not substantially constitute a right triangle, according to the cosine theorem, the opposite side (i.e., the measurement distance between the border and the reference point) may be calculated, given that the border distance and the reference distance are two adjacent sides, and an angle between the border direction and the reference direction is provided.

In an embodiment, the control module 13 further contains an edge determining unit 136 which is electrically connected to the border detection unit. The edge determining unit 136 may be arranged to calculate the ratio of the second distance $d_2$ and the reference distance $d_0$. If the ratio is greater than the ratio threshold, it is determined that an edge is detected. If the ratio is not greater than the ratio threshold, it is determined that no edge is detected. For example, when the length measurement device 1 is arranged for measuring the height of the subjects (i.e., the pupils) in an elementary school, the operator puts the length measurement device 1 1.5 meters in front of the subjects (i.e., the pupils). In general, the pupils' height seldom exceeds 1.8 meters, and thus the distance between the length measurement device 1 and the pupils' head should be less than 2.4 meters. At this moment, ratio threshold may be set to 1.6 (i.e., the ratio of 2.4/1.5). When the ratio of the second distance $d_2$ and the reference distance is detected to be greater than 1.6, the edge determining unit 136 determines an edge is detected.

In an embodiment, the edge determining unit 136 may be arranged to calculate the absolute value of the difference of the second distance $d_2$ and a first distance $d_1$. If the absolute value of the difference is greater than a variation threshold, it is determined that an edge is detected. If the absolute value of the difference is not greater than the variation threshold, it is determined that no edge is detected. To be more specifically, if the difference of the second distance $d_2$ and the first distance $d_1$ falls in a range (e.g., −30 centimeters to 30 centimeters), it is determined that no edge is detected. If the difference falls out of the range, it is determined that an edge is detected.

In practice, because the figures of the subjects (e.g., children, adults, elders, pregnant ladies) vary in prominent proportions, the aforementioned variation threshold may be adjusted according to different subjects. For example, when it comes to measuring a child's height, the variation threshold may be set to 20 centimeters, while to measuring the height of a subject with an obesity disorder, the variation threshold may be set to 60 centimeters.

In an embodiment, the control module 13 may further includes a threshold calculation unit 137 which is electrically connected to the border detection unit 133. The threshold calculation unit 137 may calculate the variation threshold according to the first distance $d_1$, the measurement direction and the first angle θ. For example, since the human body is substantially 30 to 50 centimeters thick, if the second distance $d_2$ multiplies the cosine value of the rotated measurement direction and then minuses the first distance $d_1$ multiplied by the cosine value of the measurement direction yielding a length greater than 50 centimeters, it is highly likely that an edge is detected, and thus a the variation threshold may be configured accordingly.

Figure 3A:
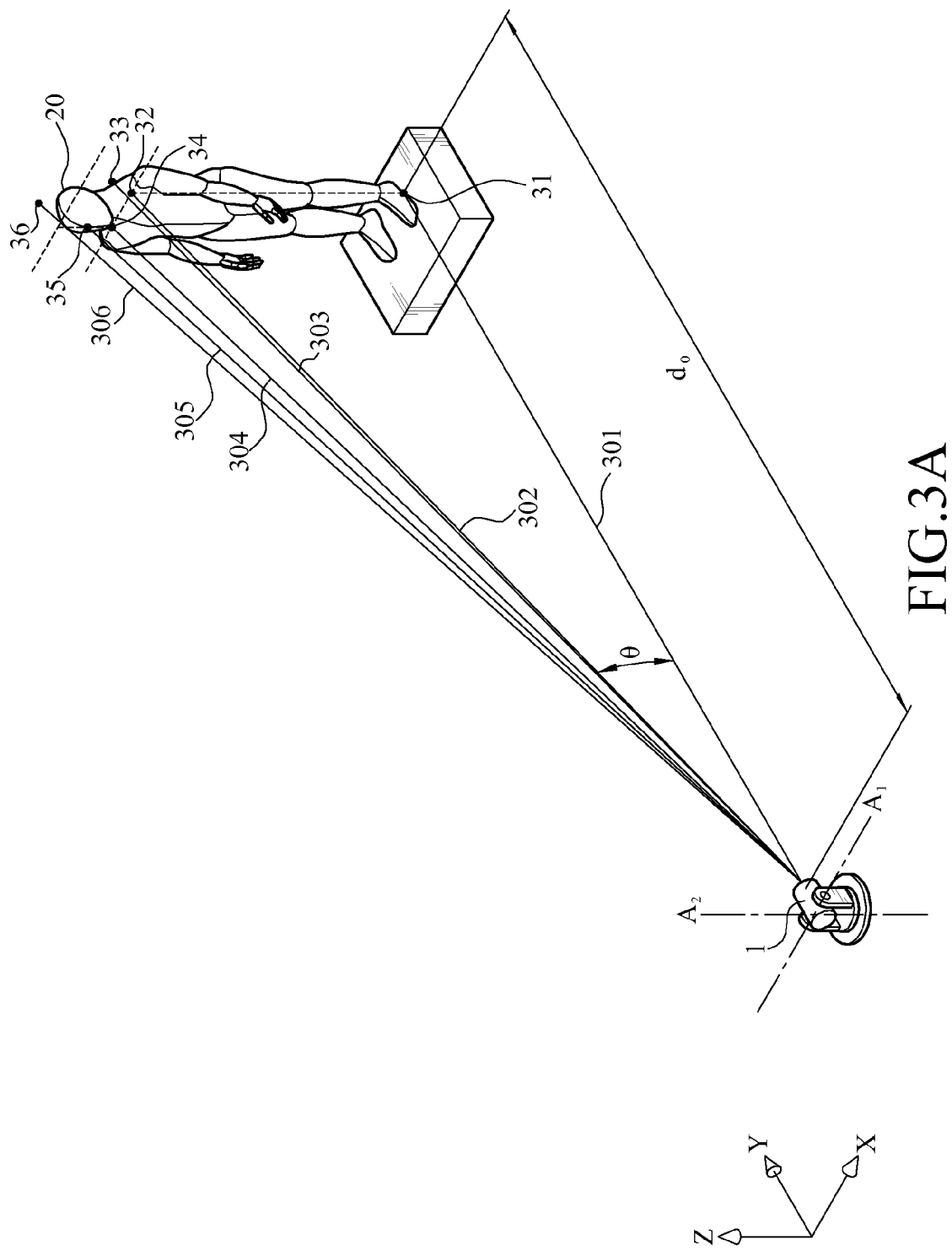
FIGS. 3A and 3B are schematic diagrams illustrating operations of the length measurement device according to an embodiment of the present invention.
Figure 3B:
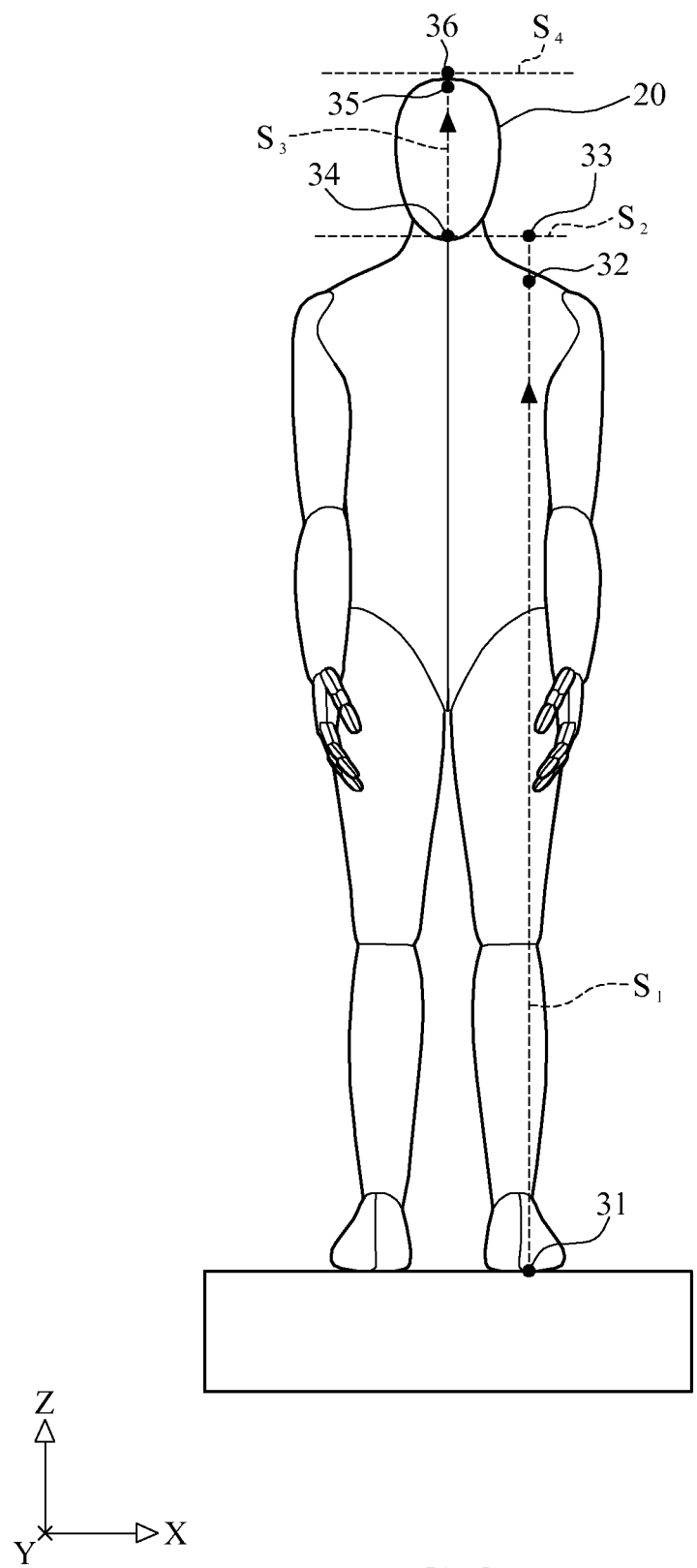

In an embodiment, the control module 13 may further includes a border determining unit 138 which is electrically connected to the border detection unit 133. The border determining unit 138 is arranged to execute a border determining procedure. Please concurrently refer to FIGS. 3A and 3B, which are schematic diagrams illustrating operations of the length measurement device according to an embodiment of the present invention. As shown in FIG. 3A, the length measurement device 1 first emits the laser onto the reference point 31 on the feet of the user 30 in the reference direction 301 for detecting the reference distance $d_0$. Then the length measurement device 1 start rotating a certain angle multiple times around the X axis (i.e., the first axis A1) such that the measurement direction moves upward along a scan line S1 paralleled with the Z axis (i.e., the first detecting direction) and emits the laser after each rotation to measure the distance. When the length measurement device 1 emits the laser onto a reflection point 32 on the surface of the user's shoulder in the measurement direction 302, next time the length measurement device 1 will emit the laser onto a reflection point 33 on the wall behind the user in the measurement direction 303. Since the aforementioned method determines whether an edge exists, the border determining unit 138 of the length measurement device 1 will execute the border determining procedure, and thus starts to scan laterally along a scan line S2, and finds a reflection point 34 on the user's neck, in the measurement direction 304. Since the difference of the distance between the reflection point 34 and the length measurement device 1 and the distance between the reflection point 32 and the length measurement device 1 is not greater than the variation threshold, and thus it is determined that it is not yet reached the border (i.e., the head) of the subject (i.e., the user).

To sum up, the control module 13 and the multiple units comprised therein may be realized by application-specific integrated circuit (ASIC), advanced RISC machine (ARM), central processing unit (CPU), single-chip control device or other equipments opt for executing computing and control command, the embodiment is not limited hereinafter.

Then starting with the measurement direction 304, the length measurement device 1 emits the laser multiple times vertically upward along the scan line S3. When the length measurement device 1 emits the laser onto a reflection point 35 on the surface of the user's forehead in the measurement direction 305, next time the length measurement device 1 will emits the laser onto a reflection point 36 on the wall behind the user in the measurement direction 306. Since the aforementioned method determines whether an edge exists, the border determining unit 138 of the length measurement device 1 executes the border determining procedure, and scans laterally along scan line S4. After the scanning, a border is determined between the measurement direction 305 and the measurement direction 306. Therefore, the reflection point 35 may be selected as a border, the border is further determined in between the reflection point 35 and reflection point 36.

Figure 4A:
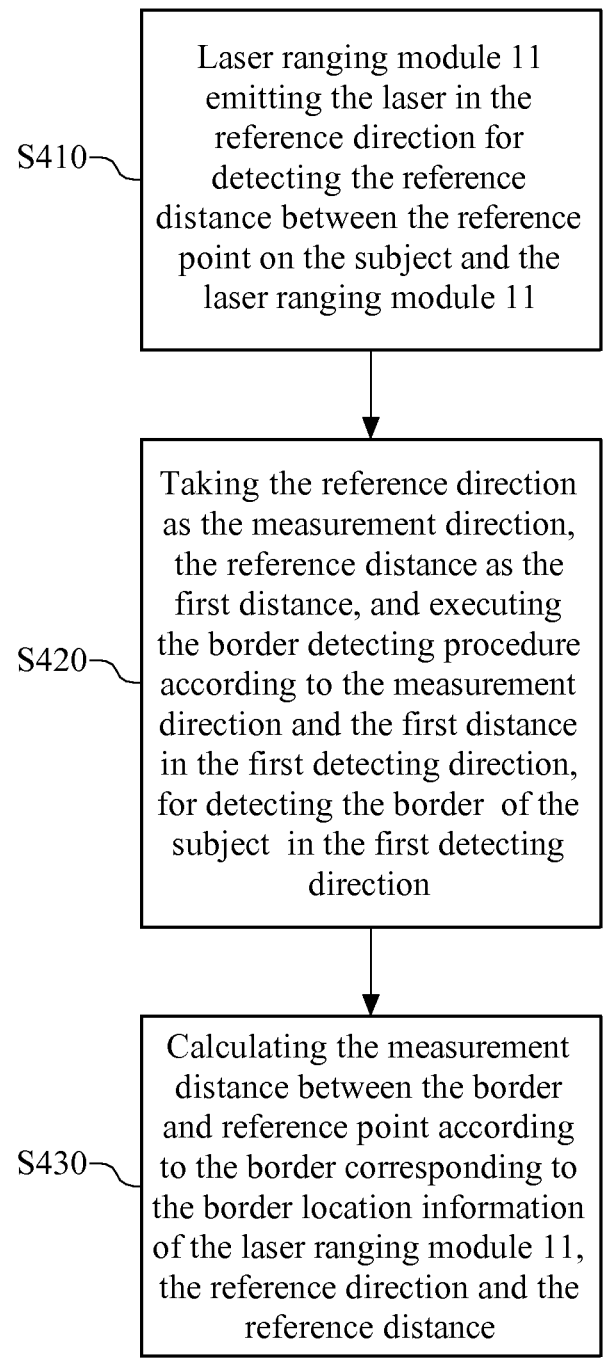
FIG. 4A is a flowchart of a length measurement method according to an embodiment of the present invention.

Please concurrently refer to FIGS. 1 and 4A, FIG. 4A is a flowchart of a length measurement method according to an embodiment of the present invention. As shown in S410, the ranging unit 131 controls the laser ranging module 11 emitting the laser in the reference direction for detecting the reference distance between the reference point on the subject and the laser ranging module 11. As shown in S420, the border detection unit 133 uses the reference direction as the measurement direction, the reference distance as the first distance, and executes the border detecting procedure according to the measurement direction and the first distance in the first detecting direction (e.g., from head to feet), for detecting the border of the subject in the first detecting direction. As shown in S430, the border detection unit 133 calculates the measurement distance between the border and reference point according to the border corresponding to the border location information of the laser ranging module 11, the reference direction and the reference distance.

Figure 4B:
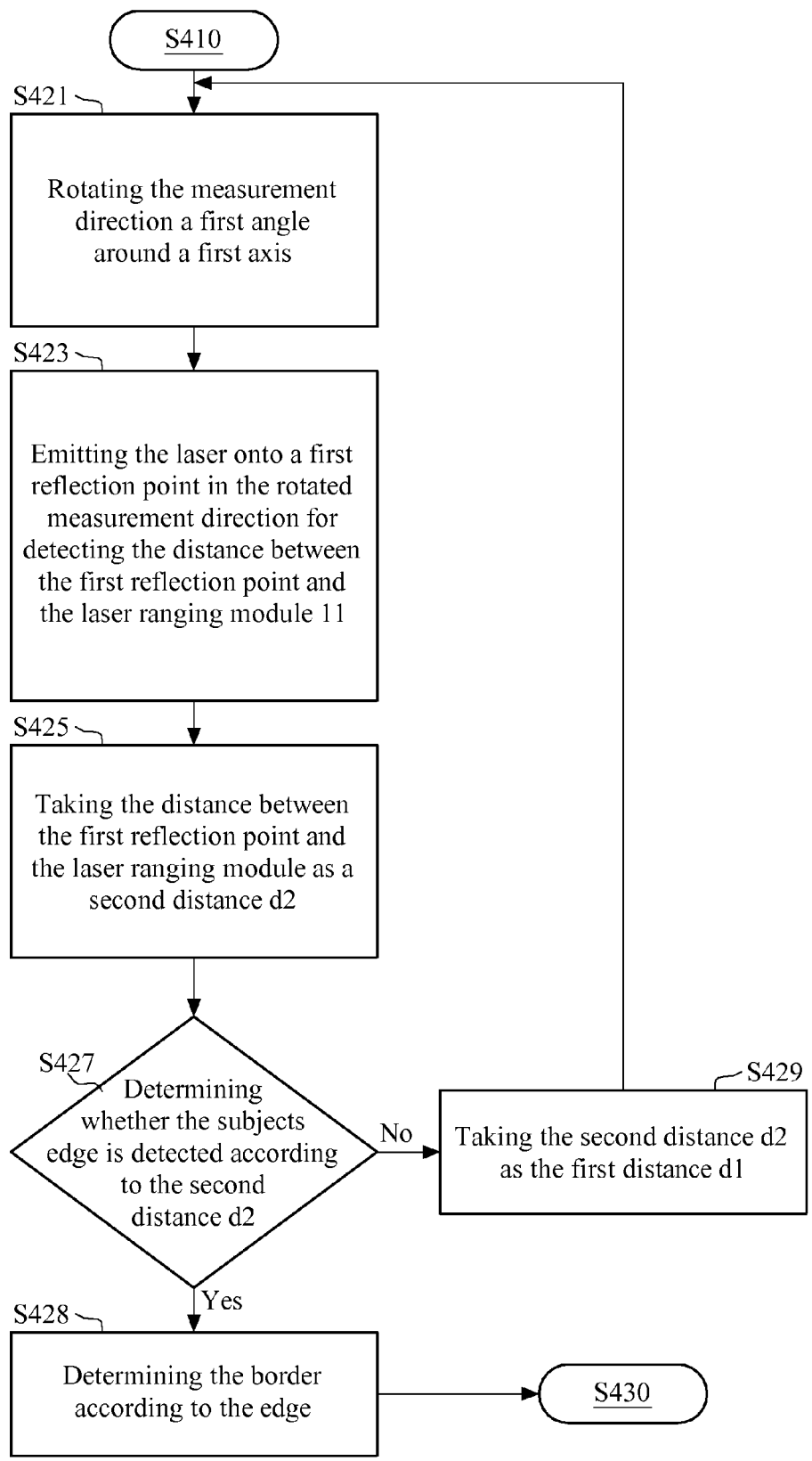
FIG. 4B is a flowchart of a border detecting procedure method according to an embodiment of the present invention.

Regarding the border detecting procedure, please refer to FIG. 4B, which is a flowchart of a border detecting procedure method according to an embodiment of the present invention. As shown in S421, the border detection unit 133 rotates the measurement direction a first angle θ around a first axis. As shown in S423, the border detection unit 133 controls the laser ranging module 11 emits the laser onto a first reflection point in the rotated measurement direction for detecting the distance between the first reflection point and the laser ranging module 11. As shown in S425, the border detection unit 133 uses the distance between the first reflection point and the laser ranging module as a second distance $d_2$. As shown in S427, the border detection unit 133 determines whether the subject's edge is detected according to the second distance $d_2$. If there is an edge detected, as shown in S428, the border is determined according to the edge. If there is no edge detected, as shown in S429, the border detection unit 133 uses the second distance $d_2$ as the first distance $d_1$, and then goes back to S421, and continues executing the border detecting procedure in the first detecting direction for detecting the subject's border.

In an embodiment, in S428, the border is determined by directly taking the edge as the border. In this embodiment, the measurement direction is uses as the border direction in the aforementioned border location information, and the present first distance is used as the border distance.

In an embodiment, S428 may include steps of dividing the angle between the rotated measurement direction and the original measurement direction into one or more sub-angle to obtain at least one measurement direction. Therefore, each measurement direction is in between the rotated measurement direction and the original measurement direction. S428 may also include steps of controlling the laser ranging module 11 emits the laser multiple time in the aforementioned measurement directions, so as to further determine the location of the edge, and determine the border according to edge.

Figure 4C:
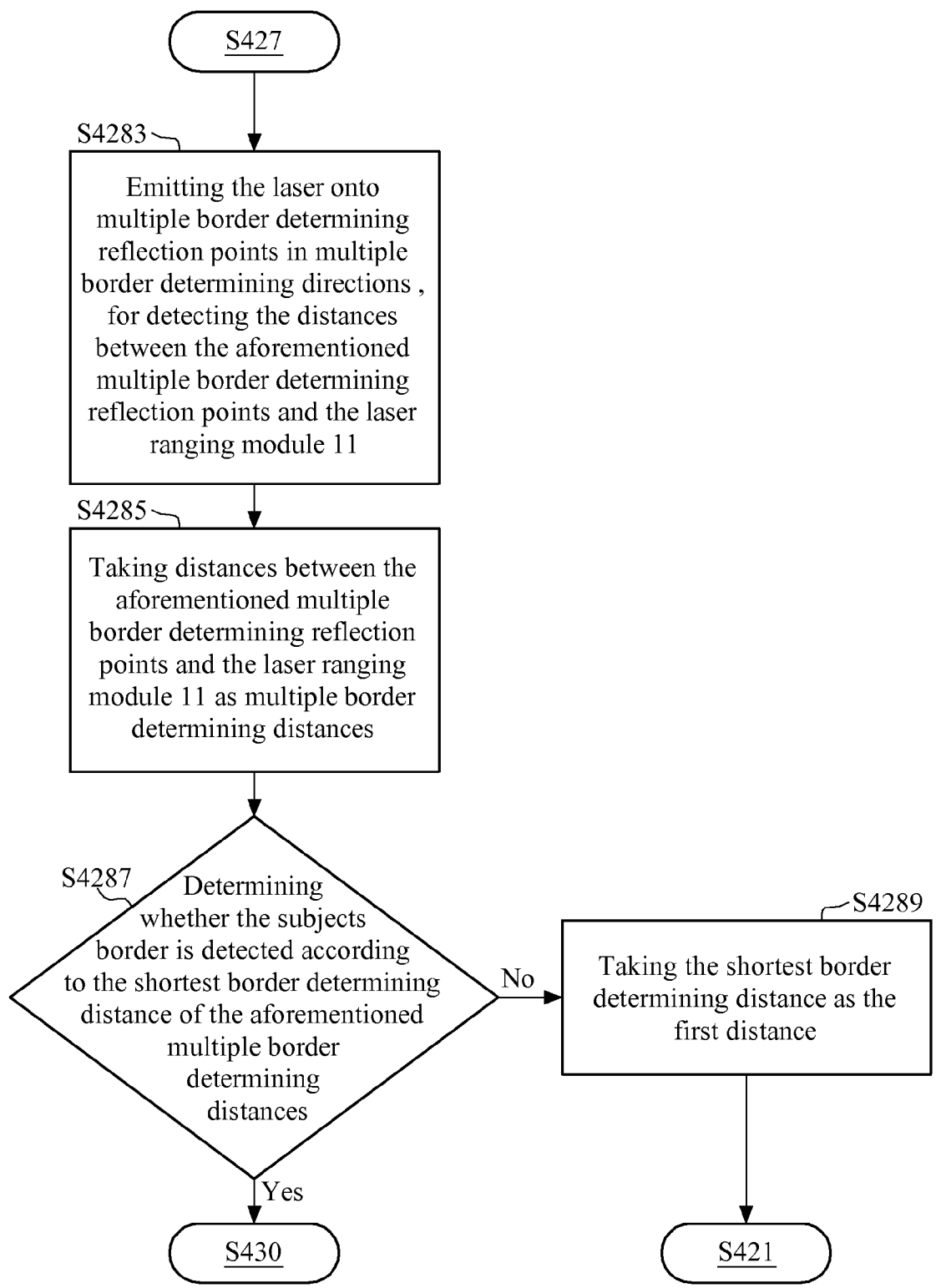
FIG. 4C is a flowchart of a border determining procedure method according to an embodiment of the present invention.

In another embodiment, S428 may include steps of executing a border determining procedure. Regarding the process of the border determining procedure process, please refer to FIG. 4C and FIG. 3, wherein FIG. 4C is a flowchart of a border determining procedure method according to an embodiment of the present invention. As shown in S4283, the border determining unit 138 rotates around second axis A2 (i.e., the Z axis in this embodiment), and the laser ranging module 11 emits the laser onto multiple border determining reflection points in multiple border determining directions (lateral in this embodiment, that is directions paralleled with the X axis) starting from the reflection point 33, for detecting the distances between the aforementioned multiple border determining reflection points and the laser ranging module 11. As shown in S4285, the border determining unit 138 uses distances between the aforementioned multiple border determining reflection points and the laser ranging module 11 as multiple border determining distances. As shown in S4287, the border determining unit 138 determines whether the subject's border is detected according to the shortest border determining distance (distance measured in the measurement direction 304 in this embodiment) of the aforementioned multiple border determining distances. If there is no border is detected, as shown in S4289, the border determining unit 138 uses the shortest border determining distance as the first distance, and executes the border detecting procedure in the first detecting direction for detecting the subject's border.

In S4287, the step of whether the subject's border is detected according to the shortest border determining distance may be summarized as follows: calculating the absolute value of the difference of the shortest border determining distance and first distance $d_1$; if the absolute value is greater than the variation threshold, determining the border is detected; if the absolute value is not greater than the variation threshold, determining the border is not detected.

Figure 5:
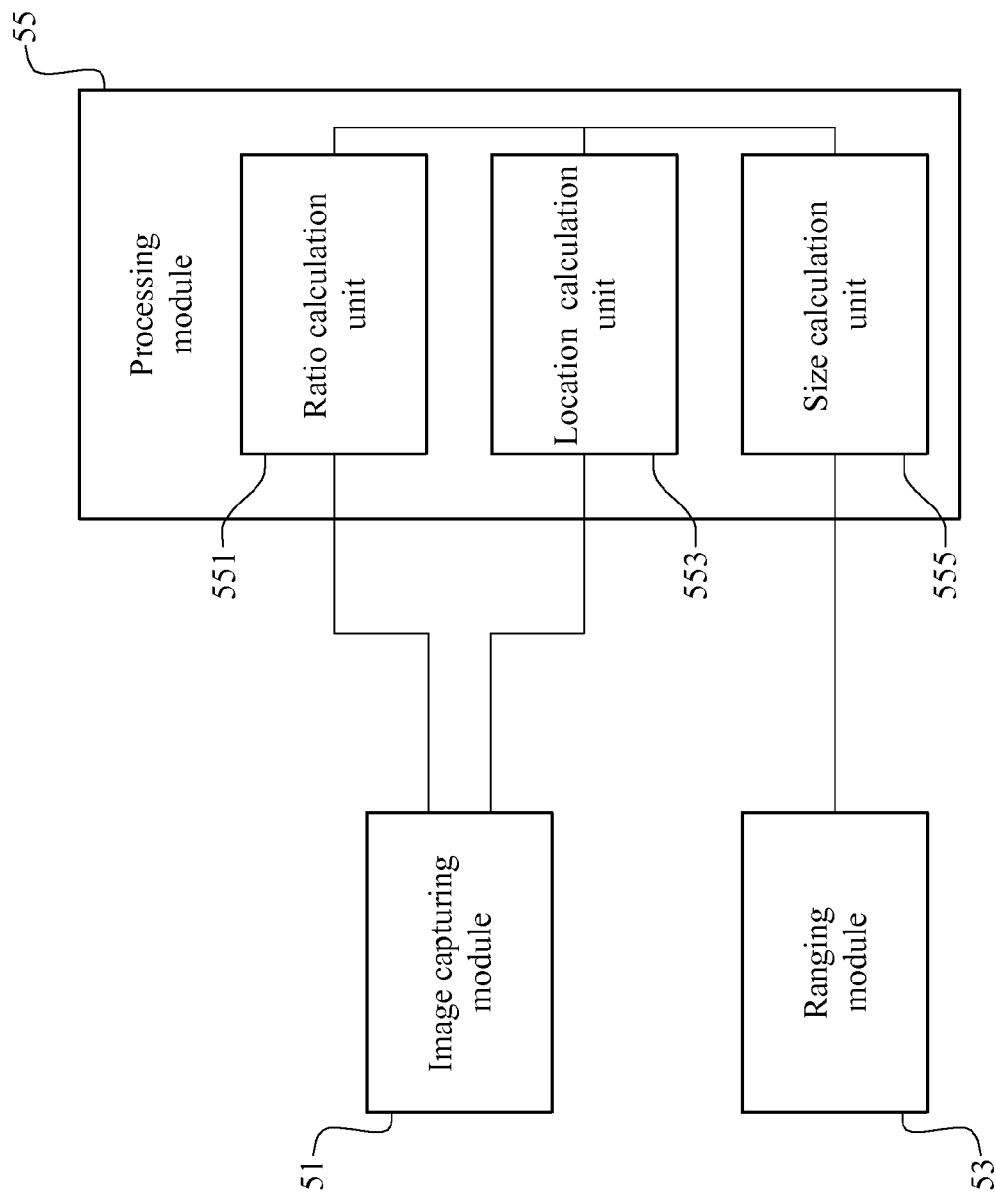
FIG. 5 is a block diagram of illustrating a length measurement device according to an embodiment of the present invention.

In another embodiment of the present invention, please refer to FIG. 5, which is a block diagram of illustrating a length measurement device according to an embodiment of the present invention. As shown in FIG. 5, the length measurement device 5 includes an image capturing module 51, a ranging module 53 and a processing module 55. The processing module 55 is electrically connected to the image capturing module 51 and the ranging module 53, respectively.

The image capturing module 51 is arranged for capturing measurement image containing the first subject. For example, the image capturing module may be a video recorder, a camera, a surveillance device, etc. that is capable of capturing image, and the present invention is not limited hereinafter.

The ranging module 53 is arranged for detecting the first measurement distance between the first subject and the image capturing module 51. Basically, the function of the ranging module 53 is to determine the first measurement distance, and then the first measurement distance may be used together with the measurement image for calculating the size of the subject. Therefore, the ranging module 53 may be an infrared ranging device, a focusing system (including face recognition module) of a camera or other device that may be arranged for detecting the first measurement distance, the present invention is not limited hereinafter.

The processing module 55 is arranged to calculate the first size of the first subject according to the first measurement distance and the measurement image. The processing module 55 may include a ratio calculation unit 551, a location calculation unit 553 and a size calculation unit 555. The ratio calculation unit 551 and the location calculation unit 553 are electrically connected to the image capturing module 51, respectively. The size calculation unit 555 is electrically connected to the ratio calculation unit 551, the location calculation unit 553 and the ranging module 53, respectively.

The ratio calculation unit 551 is arranged to calculate a first ratio of image of the first subject and the measurement image. For example, the ratio calculation unit 551 may identify a foreground object from the measurement image, and calculate how many rows of pixels the foreground object occupies in the measurement image. A vertical ratio (i.e., ratio regarding to Y axis) may be obtained according to the number of rows of pixels the foreground object occupies in the measurement image. In the same notion, a horizontal ratio (i.e., ratio regarding to X axis) may be obtained.

The location calculation unit 553 is arranged to calculate a first location of the image of the first subject in the measurement image. As mentioned above, the location calculation unit 553 is similar to the ratio calculation unit 551. The location calculation unit 553 finds the silhouette of the foreground object (i.e., the subject), and thus may obtain relevant coordinates of the subject image. The coordinates may be the coordinates of the mass center of the subject image, or may be coordinates of a nearest edge of the subject image. For example, if the image of the first subject is located at a corner of the measurement image, it is possible to present aberrations. That is, the image of the first subject will suffer distortion, and thus the following size calculation unit 555 may restore image according to aberration equations, to obtain a more accurate size of the object.

The size calculation unit 555 is arranged to calculate the first size of the first subject according to the first measurement distance, a first view angle, the first ratio and the first location. The first measurement distance and the first view angle may be stored in the meta data of the measurement image. For example, when the ranging module 53 is connected to a face recognition module of the image capturing module 51, the ranging module 53 may auto-focus one or more faces in the image, respectively, and saves the focusing information. The focusing information may translate into the measurement distance between the faces and the image capturing module 51.

To sum up, the processing module 55 and the multiple units comprised therein may be realized by application-specific integrated circuit (ASIC), advanced RISC machine (ARM), central processing unit (CPU), single-chip control device or other equipments opt for executing computing and control command, the embodiment is not limited hereinafter.

Figure 6A:
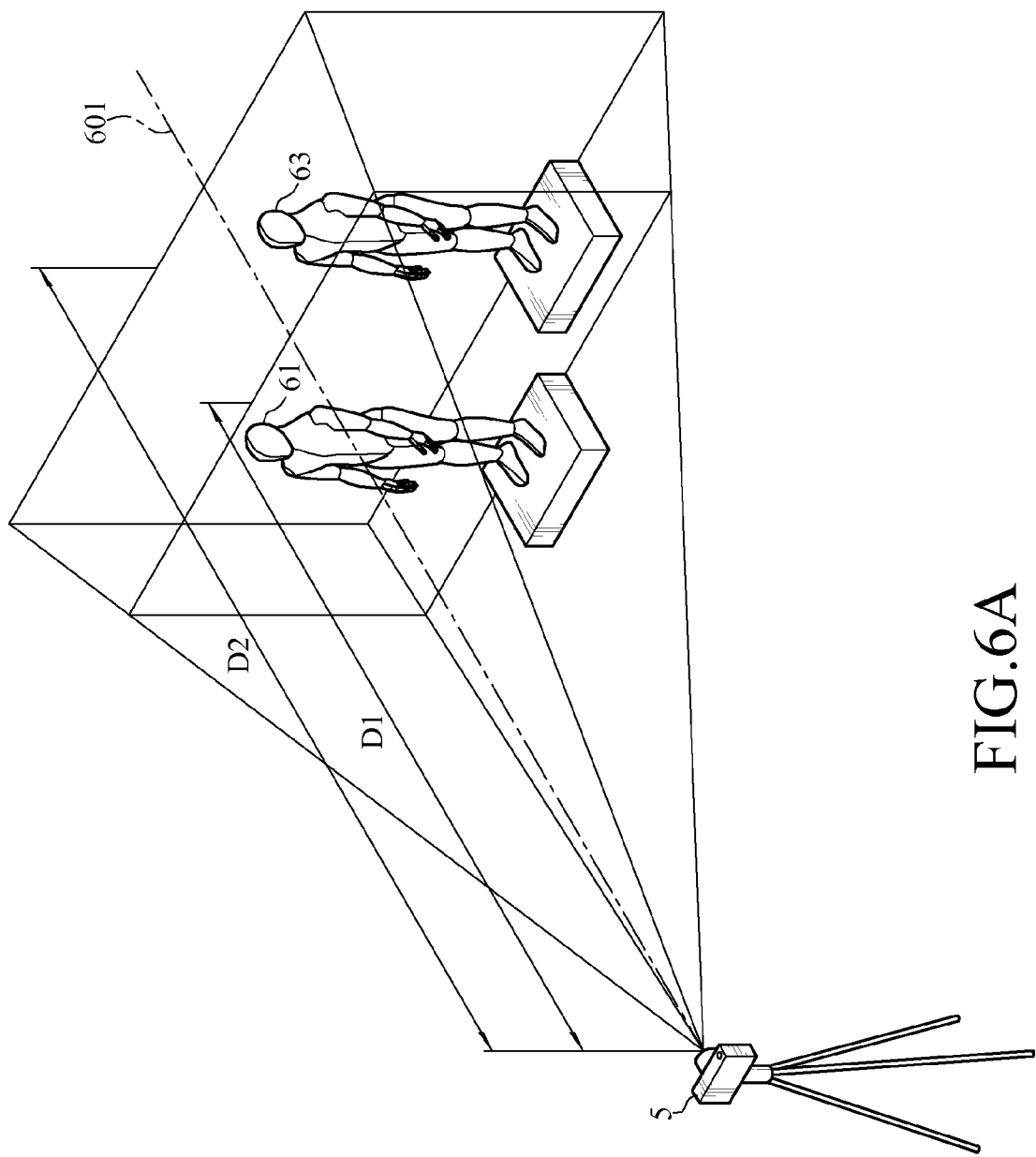
FIG. 6A is a schematic diagram illustrating operations of a length measurement device according to an embodiment of the present invention.
Figure 6B:
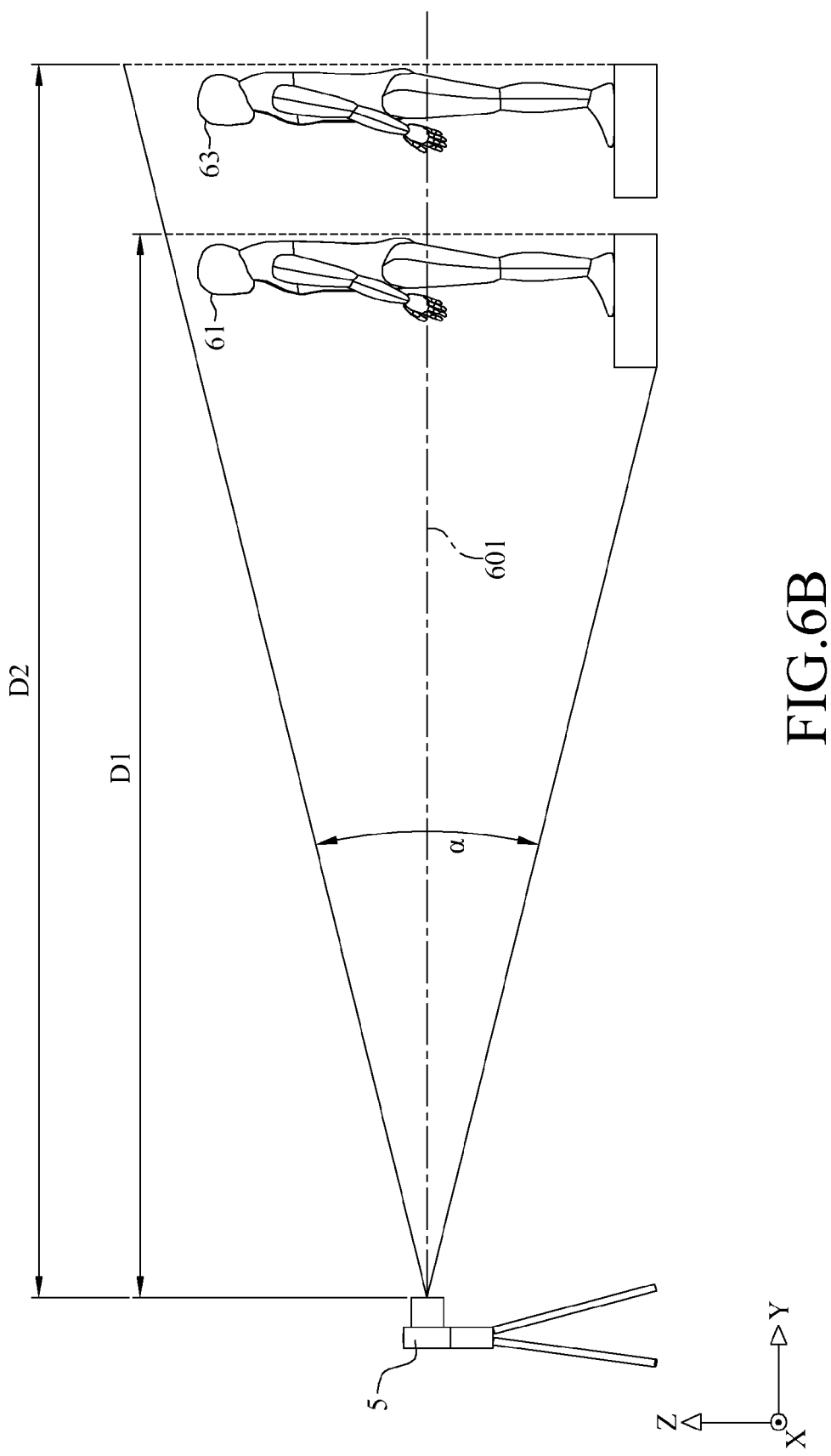
FIG. 6B is a lateral view of FIG. 6A.
Figure 6C:
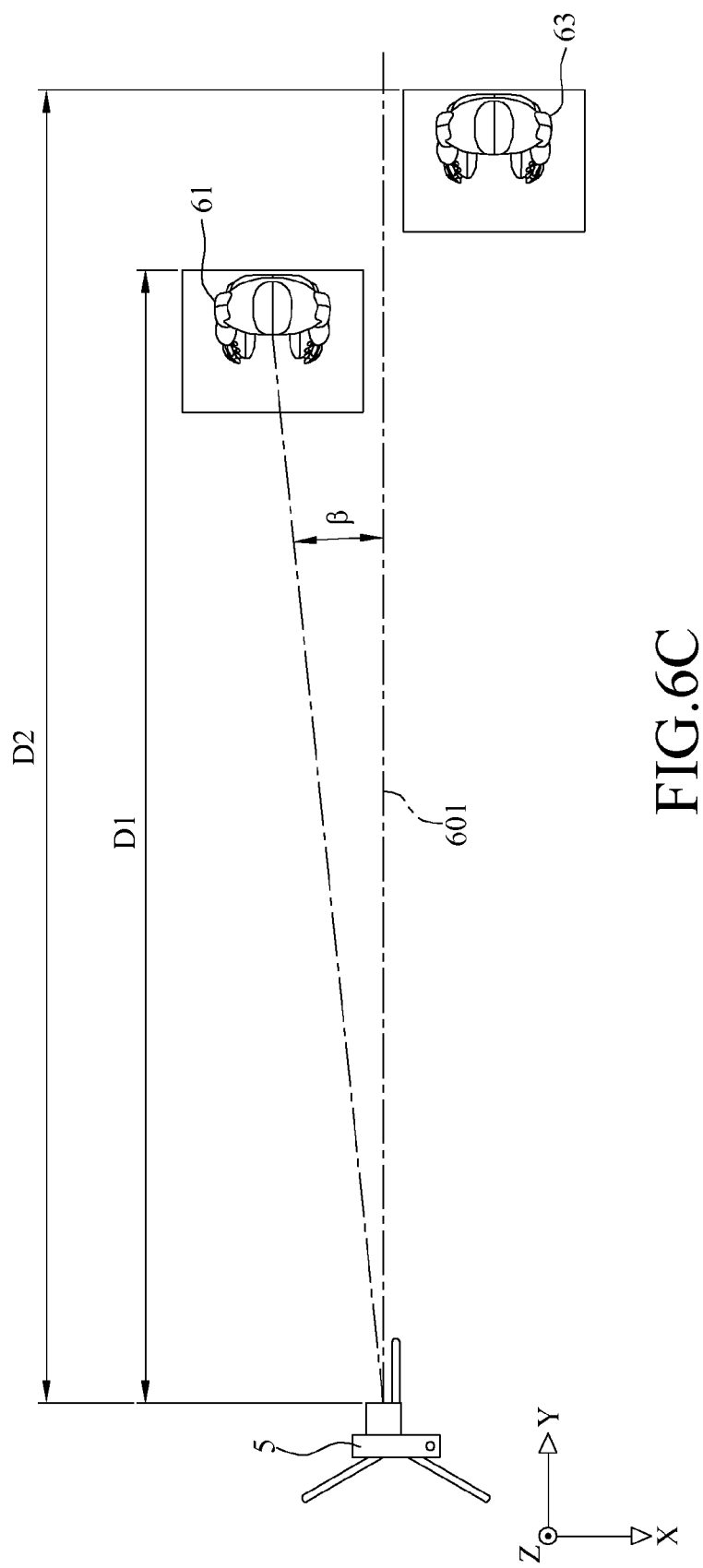
FIG. 6C is a top view of FIG. 6A.
Figure 7:
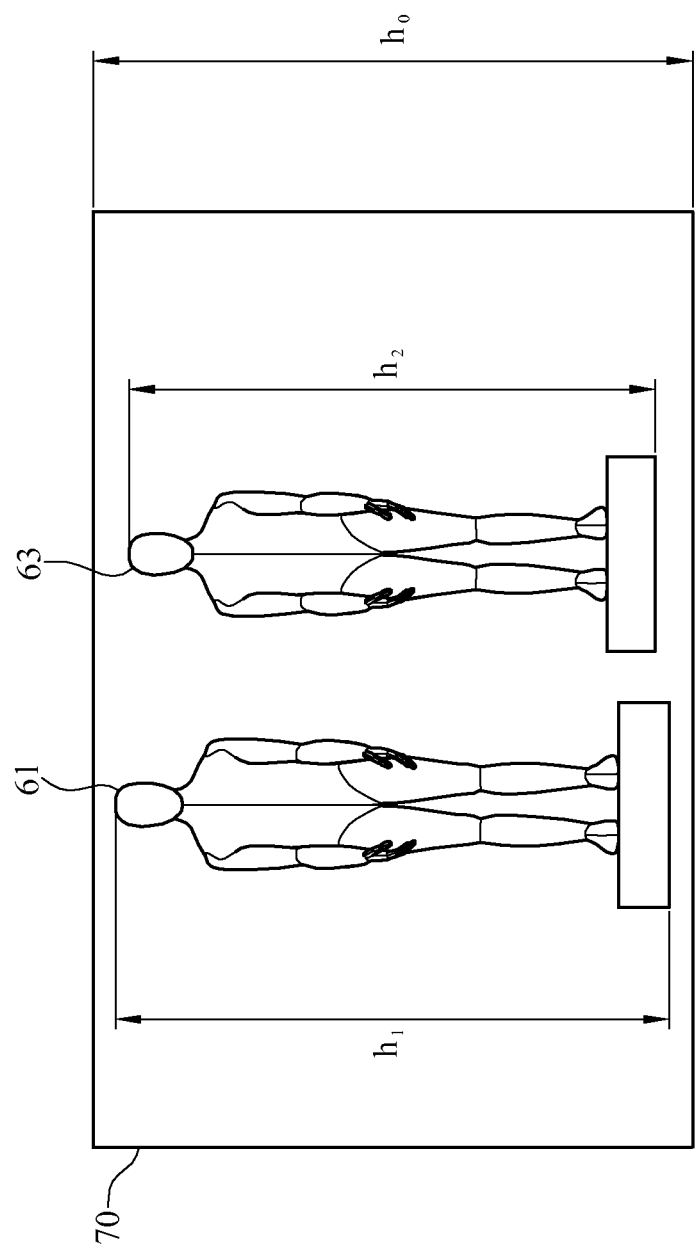
FIG. 7 illustrates measurement image corresponding to FIG. 6A.

Regarding the operations of the length measurement device according to the aforementioned embodiment of the present invention, please refer to concurrently FIG. 6A, 6B, 6C and FIG. 7. FIG. 6A to 6C are schematic diagrams illustrating operations of a length measurement device according to an embodiment of the present invention, and FIG. 7 illustrates measurement image corresponding to FIG. 6A. As shown in FIG. 6A, in an embodiment, the length measurement device 5 may capture image to a bystander 61 (i.e., the first subject), and concurrently detects the distance D1 between the plane where the bystander 61 resides and the length measurement device 5 and other relative positioning (e.g., an angle β formed between a connecting line of the bystander 61 and the length measurement device 5 and a photography axis 601 of the length measurement device 5). Then, the processing module 55 will analyze the measurement image 70, finds out image containing the bystander 61, and calculates a ratio of a height h1 (i.e., the first size) of the bystander 61 image, that is the number of the rows of pixels of the bystander 61 image occupied in the measurement image 70, and the height h0 of the measurement image 70. The height h1 of the bystander 61 may be calculated according to distance D1 (i.e., the first measurement distance), the view angle α (regarding the vertical axis) of the measurement image, the height H1 of the image of the bystander 61, the height h0 of the measurement image (i.e., the number of total rows of pixels of the measurement image 70). As shown in the following equation:

$$H_1 = \frac{h_1}{h_0} \times 2 \times D_1 \times \tan(\alpha/2)$$

In some embodiment of the present invention, if the measurement image contains multiple bystanders (i.e., the subjects), e.g. a bystander 63 (the second the subject) other than the bystander 61 in the measurement image 70. If the ranging module 53 has a face recognition module, the ranging module 53 may perform a face recognition procedure on the faces of the bystander 61 and the bystander 63, respectively. Given that, it is reasonable to concurrently store the distance D1 between the plane where the bystander 61 resides and the length measurement device 5, and the distance D2 between the plane where the bystander 63 resides and the length measurement device 5 in the meta data of the measurement image 70. The height H2 of the bystander 63 may be calculated according to the distance D2 (i.e., the second measurement distance), the view angle α (regarding the vertical axis) of the measurement image, the height h2 of the image of the bystander (i.e., the second size), that is the number of total columns of pixels of the measurement image 70, the height h0 of the measurement image. As shown in the following equation:

$$H_2 = \frac{h_2}{h_0} \times 2 \times D_2 \times \tan(\alpha/2)$$

In the length measurement device according another embodiment of the present invention, the measurement image 70 contains multiple the subjects (e.g., the bystanders 61 and 63). Since the locations of the bystanders 61 and 63 are substantially obtained, respectively, it will acquire more accurate height H1 and H2 of the bystanders 61 and 63 by aiming the photography axis of the length measurement device 5 at the bystanders 61 and 63, and repeating the above steps, height H1 and H2, respectively.

Figure 8:
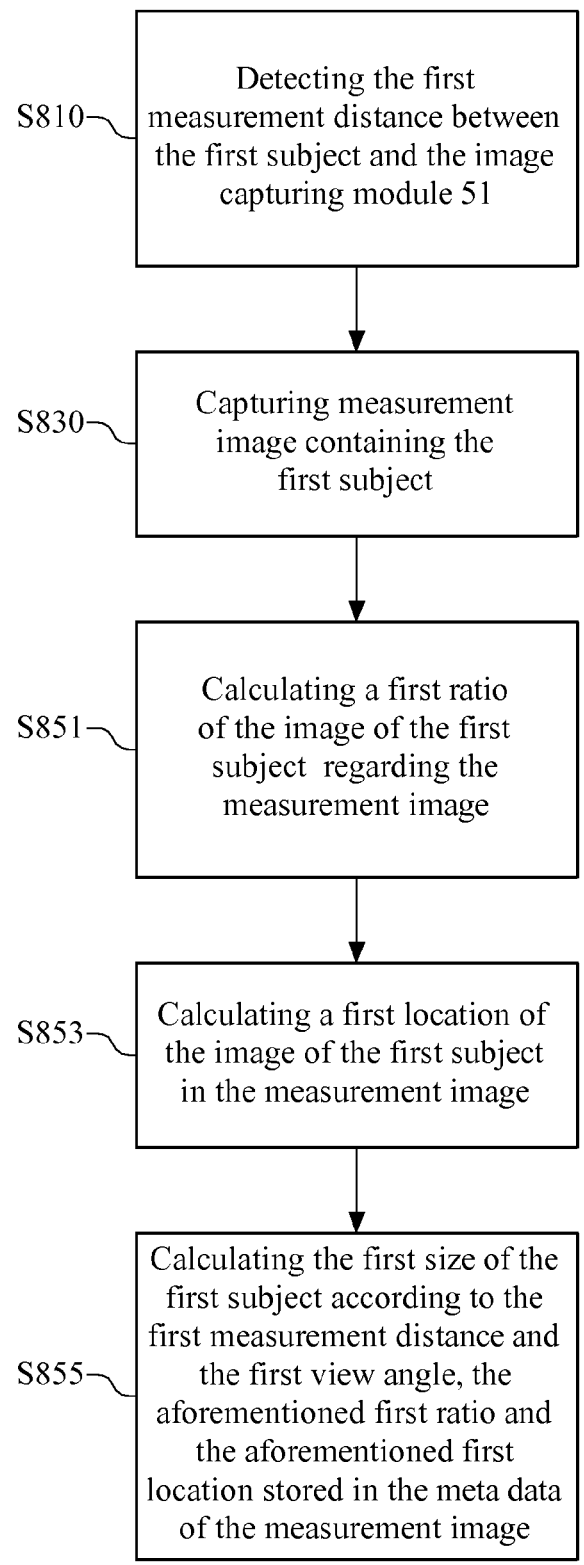
FIG. 8 is a flowchart of a length measurement method according to an embodiment of the present invention.

Regarding a length measurement method according to an embodiment of the present invention, please concurrently refer to FIGS. 5 and 8. FIG. 8 is a flowchart of a length measurement method according to an embodiment of the present invention. As shown in S810, the ranging module 53 detects the first measurement distance between the first subject and the image capturing module 51. As shown in S830, the image capturing module 51 captures measurement image containing the first subject. As shown in S851, the ratio calculation unit 551 calculates a first ratio of the image of the first subject regarding the measurement image. As shown in S853, the location calculation unit 553 calculates a first location of the image of the first subject in the measurement image. As shown in S855, the size calculation unit 555 calculates the first size of the first subject according to the first measurement distance and the first view angle, the aforementioned first ratio and the aforementioned first location stored in the meta data of the measurement image.

According to the above-mentioned multiple embodiments of the present invention, the length measurement device and the length measurement method calculate a subject's height by detecting the distance between the subject and the length measurement device and the relative positioning of the subject's head and the length measurement device. In another embodiment of the present invention, the length measurement device captures image containing the subject, detects the distance between the subject and the length measurement device, and calculates the subject's height according to the image and the distance. Therefore, according to the embodiments of the present invention, the volume of the length measurement device may be significantly decreased, and easily carried and set-up. Meanwhile, it can also obtain multiple subjects' heights rapidly.

It will be apparent to those skilled in the art that various modifications and variations can be made to the disclosed embodiments. It is intended that the specification and examples be considered as exemplary only, with a true scope of the disclosure being indicated by the following claims and their equivalents.

The invention claimed is:

1. A length measurement method, comprising:
using a laser ranging module to emit the laser in a reference direction, for detecting a reference distance between a reference point on a subject and the laser ranging module;
taking the reference direction as a measurement direction;
taking the reference distance as a first distance;

performing a border detecting procedure in a first detecting direction according to the measurement direction and the first distance for detecting a border of the subject in the first detecting direction; and calculating a measurement distance between the border and the reference point according to the border corresponding to border location information of the laser ranging module, the reference direction and the reference distance.

2. The length measurement method of claim 1, wherein the border detecting procedure comprises:

rotating the measurement direction a first angle around a first axis;

using the laser ranging module emitting the laser to a first reflection point in the rotated measurement direction, for detecting the distance between the first reflection point and the laser ranging module;

taking the distance between the first reflection point and the laser ranging module as a second distance;

determining whether an edge of the subject is detected according to the second distance;

determining the border according to the edge if the edge is detected; and taking the second distance as the first distance, performing the border detecting procedure in the first detecting direction for detecting the border of the subject if the edge is not detected.

3. The length measurement method of claim 2, wherein the step of determining the border according to the edge if the edge is detected comprises:

calculating a ratio of the second distance and the reference distance;

determining the edge is detected if the ratio is greater than a ratio threshold; and determining no edge is detected if the ratio is not greater than the ratio threshold.

4. The length measurement method of claim 2, wherein the step of determining whether the edge of the subject is detected according to the second distance comprises:

calculating an absolute value of a first difference between the second distance and the first distance;

determining the edge is detected if the absolute value of the first difference is greater than a variation threshold; and determining no edge is detected if the absolute value of the first difference is not greater than the variation threshold.

5. The length measurement method of claim 4, wherein the step of determining whether the edge of the subject is detected according to the second distance further comprises:

calculating the variation threshold according to the first distance, the measurement direction and the first angle.

6. The length measurement method of claim 2, wherein the border determining procedure comprises:

rotating around a second axis, and using the laser ranging module to emit the laser to multiple border determining reflection points in multiple border determining directions, for detecting distances between these border determining reflection points and the laser ranging module, these border determining directions are in line with a second detecting direction;

taking the distances between these border determining reflection points and the laser ranging module as multiple border determining distances;

determining whether the border of the subject is detected according to the shortest border determining distance of these border determining distances; and taking the shortest the border determining distance as the first distance, and performing the border detecting procedure for detecting the border of the subject if no border is detected.

7. The length measurement method of claim 6, wherein the step of determining whether the border of the subject is detected according to the shortest border determining distance of these border determining distances comprises:

calculating an absolute value of a second difference between the shortest the border determining distance and the second distance; and determining the border is detected if the absolute value of the second difference is greater than a variation threshold; and determining no border is detected if the absolute value of the second difference is not greater than the variation threshold.

8. The length measurement method of claim 1, wherein the border location information comprises a border direction from the laser ranging module to the border, and the step of calculating a measurement distance between the border and the reference point according to the border corresponding to border location information of the laser ranging module, the reference direction and the reference distance comprises:

calculating a angle formed by the border direction and the reference direction; and calculating the measurement distance according to the angle and the reference distance.

9. The length measurement method of claim 1, wherein the step of calculating a measurement distance between the border and the reference point according to the border corresponding to border location information of the laser ranging module, the reference direction and the reference distance comprises:

calculating the measurement distance according to the border distance and the reference distance.

10. A length measurement device, comprising:

a laser ranging module; and a control module, electrically connected to the laser ranging module, the control module comprising:

a ranging unit, electrically connected to the laser ranging module, arranged to control the laser ranging module to emit the laser in a reference direction, for detecting a reference distance between a reference point on a subject and the laser ranging module;

a border detection unit, electrically connected to the ranging unit, arranged to take the reference direction as a measurement direction, the reference distance as a first distance, and performing a border detecting procedure in a first detecting direction for detecting a border of the subject in the first detecting direction; and a calculation unit, electrically connected to the ranging unit and the border detection unit, arranged to calculate a measurement distance between the border and the reference point according to the border corresponding to border location information of the laser ranging module, the reference direction and the reference distance.

11. The length measurement device of claim 10, wherein the border detecting procedure comprises:

rotating the measurement direction a first angle around a first axis;

using the laser ranging module emitting the laser to a first reflection point in the rotated measurement direction, for detecting the distance between the first reflection point and the laser ranging module;

taking the distance between the first reflection point and the laser ranging module as a second distance;

determining whether an edge of the subject is detected according to the second distance;

determining the border according to the edge if the edge is detected; and taking the second distance as the first distance, performing the border detecting procedure in the first detecting direction for detecting the border of the subject if the edge is not detected.

12. The length measurement device of claim 11, wherein the control module further comprises a edge determining unit, electrically connected to the border detection unit, and arranged for calculating a ratio of the second distance and the reference distance, determining the edge is detected if the ratio is greater than a ratio threshold, and determining no edge is detected if the ratio is not greater than the ratio threshold.

13. The length measurement device of claim 11, wherein the control module further comprises a edge determining unit, electrically connected to the border detection unit, arranged for calculating an absolute value of a first difference between the second distance and the first distance, determining the edge is detected if the absolute value of the first difference is greater than a variation threshold, and determining no edge is detected if the absolute value of the first difference is not greater than the variation threshold.

14. The length measurement device of claim 13, wherein the control module further comprises a threshold calculation unit, electrically connected to the edge determining unit, arranged for calculating the variation threshold according to the first distance, the measurement direction and the first angle.

15. The length measurement device of claim 11, wherein the control module further comprises a border determining unit, electrically connected to the border detection unit, arranged for performing a border determining procedure to determine the border, the border determining procedure comprises:

rotating around a second axis, and using the laser ranging module to emit the laser to multiple border determining reflection points in multiple border determining directions, for detecting distances between these border determining reflection points and the laser ranging module, these border determining directions are in line with a second detecting direction;

taking the distances between these border determining reflection points and the laser ranging module as multiple border determining distances;

determining whether the border of the subject is detected according to the shortest border determining distance of these border determining distances; and taking the shortest the border determining distance as the first distance, and performing the border detecting procedure for detecting the border of the subject if no border is detected.

16. The length measurement device of claim 15, wherein the step of determining whether the border of the subject is detected according to the shortest border determining distance of these border determining distances comprises:

calculating an absolute value of a second difference between the shortest the border determining distance and the second distance; and determining the border is detected if the absolute value of the second difference is greater than a variation threshold; and determining no border is detected if the absolute value of the second difference is not greater than the variation threshold.

* * * * *